US010660571B2

(12) United States Patent
West et al.

(10) Patent No.: US 10,660,571 B2
(45) Date of Patent: May 26, 2020

(54) THERMOCHROMIC FABRICS UTILIZING CHOLESTERIC LIQUID CRYSTAL MATERIAL

(71) Applicants: John L. West, Hartville, OH (US); Yijing Chen, Hudson, OH (US); Peter Palffy-Muhoray, Kent, OH (US); Lawrence Osher, Beachwood, OH (US); Vincent J. Hetherington, Strongsville, OH (US); Jill S. Kawalec, Medina, OH (US)

(72) Inventors: John L. West, Hartville, OH (US); Yijing Chen, Hudson, OH (US); Peter Palffy-Muhoray, Kent, OH (US); Lawrence Osher, Beachwood, OH (US); Vincent J. Hetherington, Strongsville, OH (US); Jill S. Kawalec, Medina, OH (US)

(73) Assignee: KENT STATE UNIVERSITY, Kent, OH (US)

( * ) Notice: Subject to any disclaimer, the term of this patent is extended or adjusted under 35 U.S.C. 154(b) by 0 days.

(21) Appl. No.: 14/576,761

(22) Filed: Dec. 19, 2014

(65) Prior Publication Data
US 2015/0173679 A1 Jun. 25, 2015

Related U.S. Application Data

(60) Provisional application No. 61/918,389, filed on Dec. 19, 2013.

(51) Int. Cl.
*A61B 5/00* (2006.01)
*A61B 5/01* (2006.01)
*A61F 13/84* (2006.01)

(52) U.S. Cl.
CPC ............ *A61B 5/6807* (2013.01); *A61B 5/015* (2013.01); *A61B 5/6803* (2013.01); *A61F 13/84* (2013.01)

(58) Field of Classification Search
CPC ......... A61B 5/6807; A61B 5/01; A61B 5/015; A61B 5/6801; A61B 5/6802; A61B 5/6804
See application file for complete search history.

(56) References Cited

U.S. PATENT DOCUMENTS

| 3,619,254 | A | * | 11/1971 | Davis | B44F 1/00 252/299.7 |
| 3,796,884 | A | * | 3/1974 | Tricoire | A61B 5/015 230/316 |
| 3,847,139 | A | * | 11/1974 | Flam | A61B 5/015 349/199 |

(Continued)

*Primary Examiner* — Max F Hindenburg
(74) *Attorney, Agent, or Firm* — Renner Kenner Greive Bobak Taylor & Weber

(57) ABSTRACT

A thermochromic fabric utilizing cholesteric liquid crystals includes a fabric material or garment formed therefrom. The liquid crystal material is patterned with a plurality of different liquid crystal formulations, whereby each formulation has high thermal sensitivity over a narrow temperature range. As a result, the aggregate pattern of liquid crystal material formed on the thermochromic fabric allows the thermochromic fabric to have high thermal sensitivity over a broad temperature range. As such, the fabric or garment may be worn on specific body parts of a patient, such as his or her feet, to assist in making a medical diagnosis.

21 Claims, 3 Drawing Sheets

(56) References Cited

U.S. PATENT DOCUMENTS

| | | | | | |
|---|---|---|---|---|---|
| 4,642,250 | A | * | 2/1987 | Spector | A41D 31/00 |
| | | | | | 374/E11.022 |
| 4,650,707 | A | * | 3/1987 | Crigger | G01K 11/02 |
| | | | | | 374/E11.004 |
| 4,747,413 | A | * | 5/1988 | Bloch | A41B 13/00 |
| | | | | | 128/903 |
| 5,124,819 | A | * | 6/1992 | Davis | G01K 11/165 |
| | | | | | 349/199 |
| 6,927,316 | B1 | * | 8/2005 | Faries, Jr. | A41D 13/1245 |
| | | | | | 602/14 |
| 7,559,902 | B2 | * | 7/2009 | Ting | A61B 5/0408 |
| | | | | | 600/529 |
| 9,131,892 | B2 | * | 9/2015 | Markel | A61B 5/0015 |
| 9,186,092 | B2 | * | 11/2015 | Mestrovic | A61B 5/01 |
| 2007/0252115 | A1 | * | 11/2007 | Arehart | A41D 19/0082 |
| | | | | | 252/583 |
| 2008/0279253 | A1 | * | 11/2008 | MacDonald | A41D 13/002 |
| | | | | | 374/162 |
| 2009/0046760 | A1 | * | 2/2009 | Matheson | A41D 13/005 |
| | | | | | 374/141 |
| 2013/0263352 | A1 | * | 10/2013 | Crockett, Jr. | A41D 13/0015 |
| | | | | | 2/69 |
| 2013/0331683 | A1 | * | 12/2013 | Wehberg | A61B 5/015 |
| | | | | | 600/407 |

* cited by examiner

US 10,660,571 B2

THERMOCHROMIC FABRICS UTILIZING CHOLESTERIC LIQUID CRYSTAL MATERIAL

CROSS-REFERENCE TO RELATED APPLICATION

This application claims the benefit of U.S. Provisional Application No. 61/918,389 filed Dec. 19, 2013, the contents of which are incorporated herein by reference.

TECHNICAL FIELD

The present invention is directed to liquid crystals. In particular, the present invention relates to the use of liquid crystal material to form thermochromic fabrics to visualize the skin temperature of a person in order to conduct medical diagnoses. More particularly, the present invention relates to thermochromic fabrics patterned with different cholesteric liquid crystal formulations to achieve high thermal sensitivity over a broad temperature range.

BACKGROUND OF THE INVENTION

Cholesteric liquid crystals are well-known for their ability to change color as a function of temperature. For example, the temperature visualization feature of liquid crystals has been utilized to make various devices, such as thermometers. Cholesteric liquid crystals have also been used in the past for medical diagnostic devices. For example, the device shown in FIG. 1, was used to thermally profile a human feet (Shlens M, Stoltz M R, Benjamin A: "Orthopedic Applications of Liquid Crystal Thermography" published in the Western Journal of Medicine; volume 122, pages 367-370; May 1975). To produce such thermal response, each foot was first painted black before liquid crystal (LC) material was applied thereon as a thin viscous film or coating. However, such prior art approach is messy and time consuming to complete. Furthermore, such approach only allows for a single cholesteric formulation to be coated or applied on the person's feet, and therefore limits the temperature range and/or sensitivity of the response. Because of the inconvenience and the limited temperature range and/or sensitivity that was achievable by this approach, it was never widely adopted for use in medical diagnosis.

Cholesteric liquid crystals have also been coated on fibers to produce fabrics that change color with temperature for unique fashion applications. For example, U.S. Pat. No. 4,642,250 entitled "Fabrics and Garments Formed Thereby Having Thermally-Sensitive Chromatic Properties" discloses a technique of micro-encapsulating liquid crystals in a minute, synthetic casing. These encapsulated crystals are dispersed on yarns of a fabric and bonded thereto, so that the liquid crystals will not wash out or be dislodged from the yarns, when the fabric is washed or otherwise cleaned. However, such coated fibers have high thermal sensitivity in only a limited or narrow temperature range, as only one liquid crystal formulation is used. As a result, the usefulness of the temperature measurements provided by such coated fabrics is limited.

Therefore, there is a need for a thermochromic fabric that incorporates multiple cholesteric liquid crystal (LC) formulations each having high thermal sensitivity over a narrow or specific temperature range, so as to allow the thermochromic fabric to have a high thermal sensitivity over a broad temperature range. In addition, there is a need for a thermochromic fabric that is inexpensive, and convenient to use, such that it can be used as a diagnostic medical tool, which is suitable for direct use at home by patients, thereby allowing for the early detection of a wide variety of medical conditions. Furthermore, there is a need for a thermochromic fabric that eliminates the complications and messiness of prior art techniques, whereby patients are first painted with black ink before a film of cholesteric liquid crystal (LC) material is applied thereon.

SUMMARY OF THE INVENTION

The present invention contemplates fabric materials and garments formed therefrom that incorporate a cholesteric liquid crystal (LC) material, which changes color in accordance with a change in skin temperature, thereby allowing a caregiver to visualize the temperature profile of the human body, or portion thereof, as means of medical diagnosis. Variations in external skin temperature are an early indication of the development of a wide variety of medical conditions including tumors, infection and changes in blood circulation. Therefore, the thermochromic fabric material contemplated by the present invention can be fabricated into wearable garments, which can be used as a simple diagnostic tool that provides a visual temperature profile of all or part of a patient's body.

It is one aspect of the present invention to provide a thermochromic fabric that includes a layer of fabric material to be placed in contact with skin. At least two types of cholesteric liquid crystal materials applied to the layer of fabric, such that each of the at least two types of liquid crystal materials changes color over different temperature ranges. In addition, the liquid crystal materials change color based on the temperature of the skin.

BRIEF DESCRIPTION OF THE DRAWINGS

These and other features and advantages of the present invention will become better understood with regard to the following description, appended claims, and accompanying drawings wherein:

DETAILED DESCRIPTION OF THE INVENTION

Figure 1:
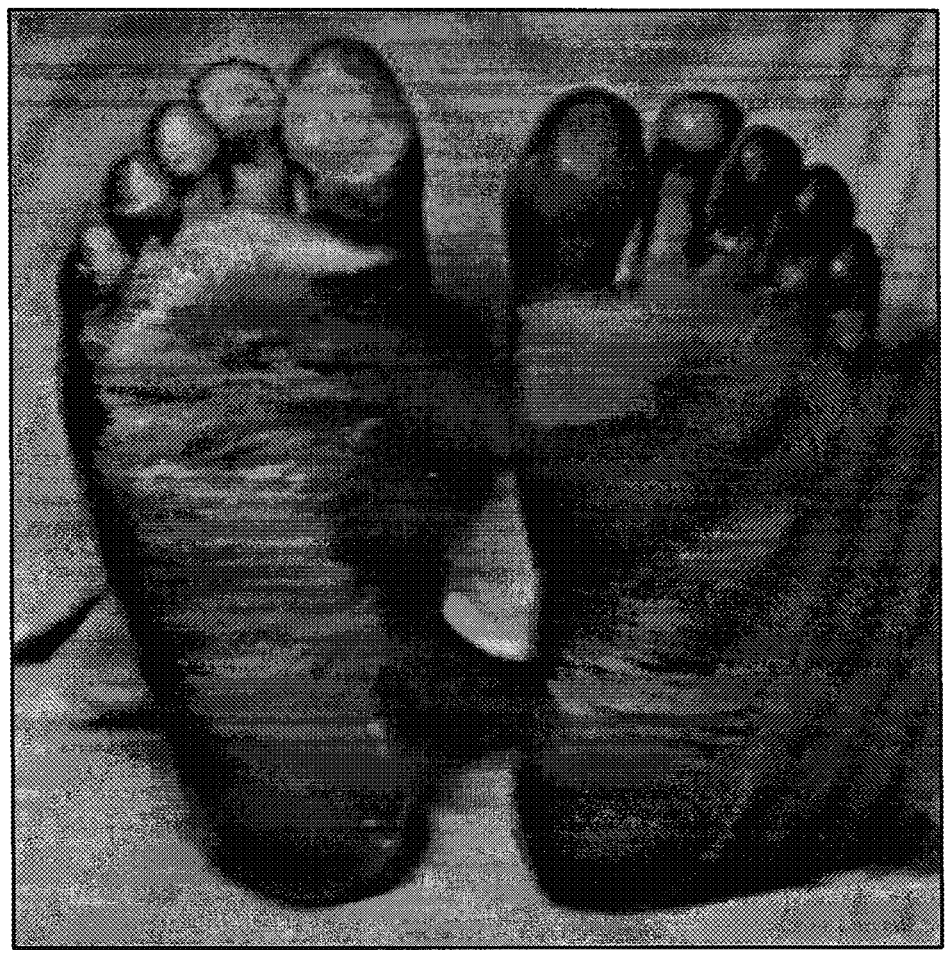
FIG. 1 is an image of thermochromic liquid crystals applied to human feet using a prior-art technique in order to generate a thermal profile image thereof (Western Journal of Medicine; volume 122, pages 367-370, May 1975)
Figure 2:
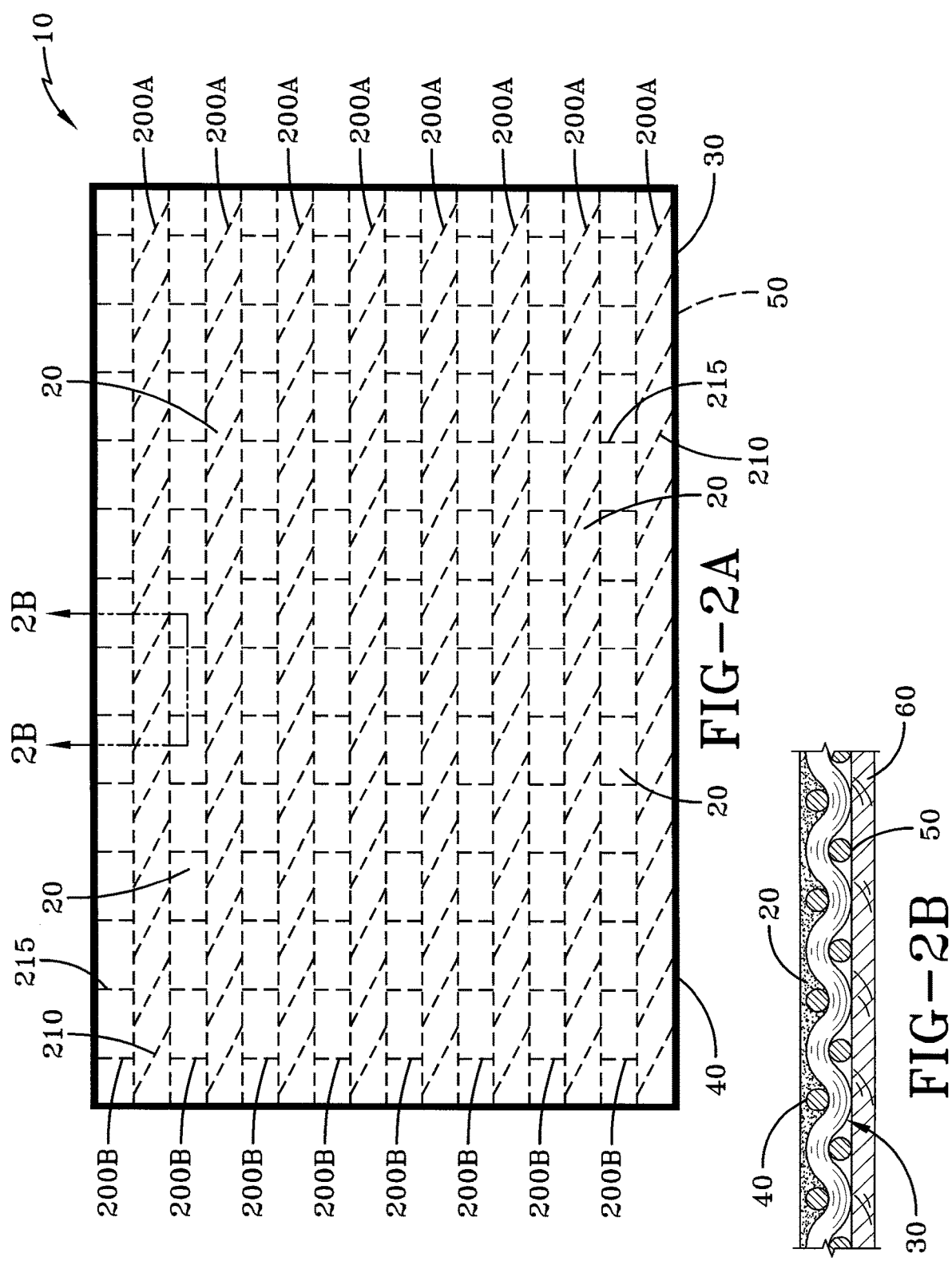
FIG. 2A is a top plan view of a thermochromic fabric having a plurality of thermal detections zones of different liquid crystal formulations in accordance with the concepts of the present invention.
FIG. 2B is a cross-sectional view of the thermochromic fabric shown in FIG. 2A in accordance with the concepts of the present invention.

A thermochromic fabric that includes a fabric material coated with a cholesteric liquid crystal (LC) material, is generally referred to by numeral 10, as shown in FIGS. 2A-B of the drawings. In one aspect, the fabric material 10 contemplated by the present invention may be draped on a patient's body, or portion thereof, or formed into garments that can be worn by the patient. As such, the present invention may be utilized as a medical diagnostic device, whereby variations in skin temperature of the patient can be visualized based on the changes in the color and/or color patterns of the liquid crystal material of the fabric/garment 10. As such, the thermochromic response produced by the fabric/garment 10 of the present invention is generated due to the treatment of the fabric/garment 10 with the cholesteric liquid crystal material.

Specifically, the thermochromic fabric 10, as shown in FIGS. 2A-B, includes liquid crystal material 20 that is disposed on a fabric material substrate 30. In particular the fabric material substrate 30 includes an outer surface 40 and an inner surface 50, which are substantially opposed to each other. As such, the liquid crystal material 20 is disposed on the outer surface 40 of the substrate 30, while the inner surface 50 of the substrate 30 is configured to be positioned adjacent to a patient's skin or body 60. Furthermore, because the liquid crystal material 20 is disposed on the outer surface 40 of the fabric material 30, the liquid crystal material 20 is not brought into direct contact with the skin or body 60 of the patient. As such, the thermally induced color change or thermochromic response of the liquid crystal material 20 of the fabric 10 is the result of the warming of the fabric material 30 by the underlying skin/body 60 of the patient. However, in some embodiments, the fabric material 10 may be configured so that the liquid crystal material 20 is in contact with the skin/body 60.

In one aspect, the fabric material 30 may comprise any suitable fabric material, such as nylon, cotton, nylon/cotton blends, and the like. In addition, the fabric material 30 may comprise any suitable color, such as black. For example, in one embodiment, the fabric material 30 may comprise tightly woven, black colored threads of nylon. As such, providing the liquid crystal material 20 on a dark-colored fabric material 30 provides enhanced contrast, and allows the change in the color or appearance of the liquid material 20 to be readily viewed by an observer. It should also be appreciated that the surfaces 40,50 of the fabric material 30 may be formed to have any desired shape or design.

Figure 3:
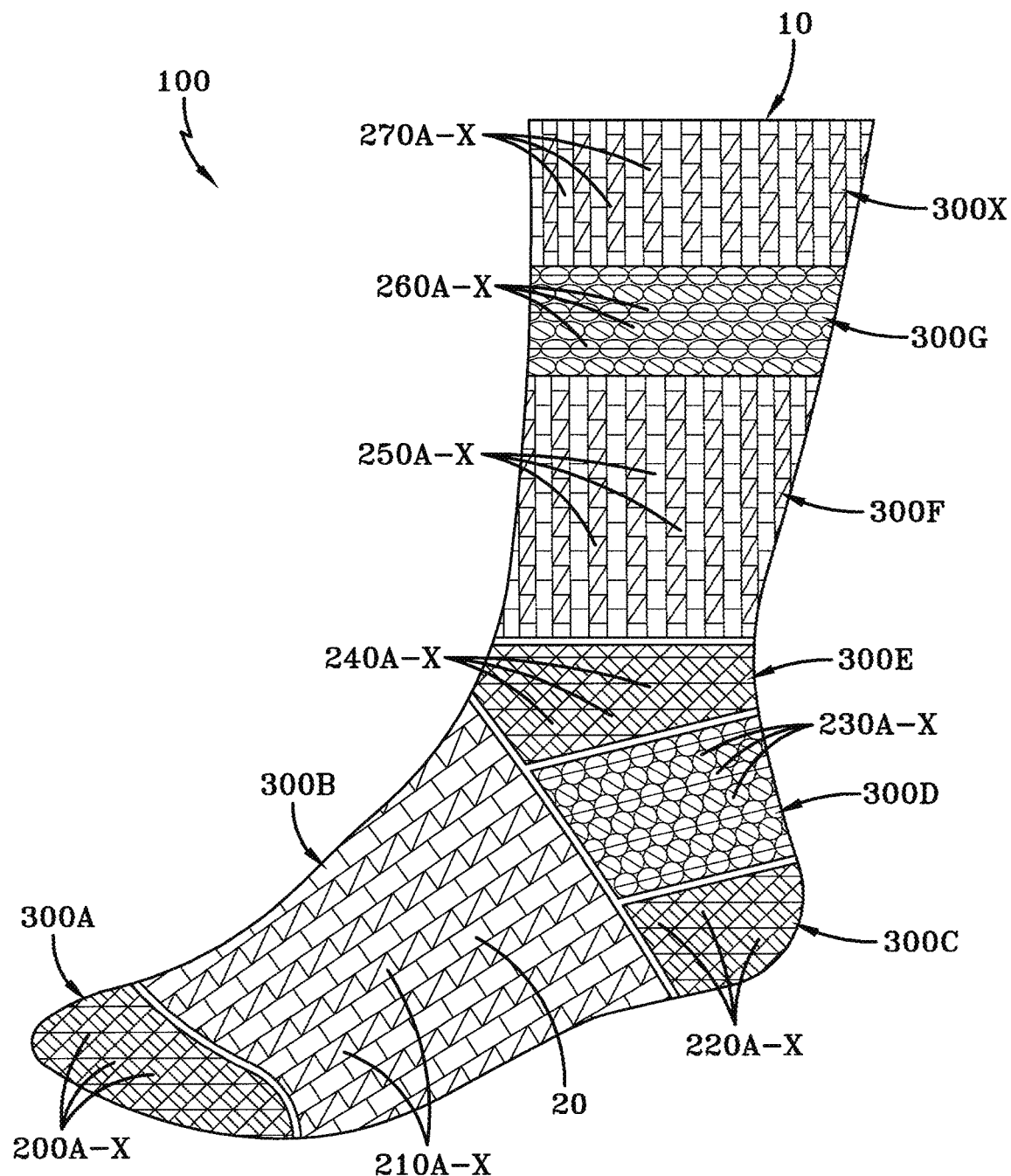
FIG. 3 is a perspective view of a garment formed from the thermochromic fabric in accordance with the concepts of the present invention.

As such, the thermochromic fabric material 10 formed of the liquid crystal material 20 and the fabric material substrate 30 may be used to form any desired wearable garment, such as form-fitting garments. For example, such wearable garment formed of the material 10 may comprise a form-fitting sock 100, as shown in FIG. 3, which can be used by to detect early signs of podiatric complications associated with diabetes for example. Because many health complications typically result in variations in foot temperature or variations in other portions of the body, the fabric of the present invention can be made into suitable garments for being worn on the particular part of the body as an early alert for a wide variety of medical complications. For example, a knee length sock could be used to visually detect signs of thrombosis in passengers on long-haul flights. Thus, the thermochromic fabric material 10 contemplated by the present invention may be used to form any desired wearable garment, such as socks, headbands, shirts, full-body suits, and the like to visualize the temperature profile of any individual body part or the entire body.

The cholesteric liquid crystal material 20 may be directly imbibed in the threads of the fabric material 30; or may be coated on the threads of the fabric material 30 as a film. Alternatively, the liquid crystal material 20 may be encased in microcapsules that are dispersed in a solvent, such as water, and a polymer binder to form a solution of liquid crystal microcapsules, which are capable of being applied and attached to the fibers of the fabric material 30. As such, the liquid crystal material 20 embodied as a solution of liquid crystal microcapsules may be applied to the fabric material 30 using any suitable technique, such as painting, screen-printing, airbrush painting, ink-jet printing, or the like.

In one aspect, with a particular selection of the cholesteric liquid crystal material formulation 20 disposed on a black-colored fabric material 30 may change from black to red, and then to blue over the range of the skin temperature to be monitored. For example, one liquid crystal material formulation that may be used by fabric 10 of the present invention may comprise a mixture of cholesterol esters. Furthermore, it should also be appreciated that the liquid crystal formulation 20 may comprise any chiral nematic liquid crystal formulation that reflects in a visible range in response to a temperature range of interest. For example, nematic liquid crystals having the properties outlined in the publication entitled "Chiral Liquid Crystals: Structures, Phases and Effects", published in Symmetry; volume 6, pages 444-472 (2014), which is incorporated herein by reference, may be used as the liquid crystal formulation 20.

In order to achieve the desired feature of high thermal sensitivity over a broad temperature range, the thermochromatic fabric 10 is configured with a plurality of different liquid crystal formulations that are each disposed in discrete or separately defined regions or zones. As such, each individual cholesteric liquid crystal formulation is applied to the fabric material 30 in a specific region or zone, such that each region or zone is positioned adjacent to another region or zone containing a different liquid crystal formulation. It should be appreciated that the regions or zones may take on any desired shape or design. As such, when two or more regions or zones are combined, the thermochromatic fabric 10 is configured to have high thermal sensitivity over a large or broad temperature range. By varying the relative concentration of the components forming the liquid crystal material 20, using known techniques, the thermochromatic response can be adjusted so that adjacent regions or zones transition through the visible color spectrum at adjacent temperature ranges. For example, a fabric material may be coated with two or more different formulations of liquid crystal materials 20, that are each contained in separate, adjacent regions or zones, which transition through a color spectrum. For practical applications, the present invention is able to monitor a broad range of temperatures that encompass a range of skin temperatures encountered in both healthy and ill individuals. For example, the present invention may be configured to detect skin temperatures within the range of about 85-105° F., although the present invention may be configured to detect any other desired temperature range. To cover such a wide range of temperatures, a plurality of different cholesteric liquid crystal formulations may be used in the fabric/garment, with each formulation being sensitive to a particular temperature range. Each of these cholesteric liquid crystal formulations may be coated as a continuous film or may be applied in particular patterns. As with a single cholesteric liquid crystal material, the variations in body temperature will be visualized as variations in color and/or variations in patterns on the fabric/garment that utilizes a plurality of cholesteric liquid crystal formulations that are sensitive to specific temperature ranges.

For example, the fabric 10 may include a zone 200A containing one liquid crystal formulation, and another zone 200B containing another liquid crystal formulation, as shown in FIG. 2A. The zones 200A-B comprise substantially rectangular sections, but may be any desired shape, and are oriented in an alternating fashion one the fabric material 30. Thus, zone 200A includes an LC formulation that is highly sensitive to a first temperature range, while adjacent zone 200B includes an LC formulation that is highly sensitive to another non-overlapping (i.e. adjacent), or nearly non-overlapping, temperature range that is above that of the zone 200A. As a result, the zones 200A-B undergo their thermochromatic responses at different temperature ranges.

It is also contemplated that each of the regions or zones 200A-B each containing a particular the liquid crystal formulation may also be configured to have different patterns to add to the ability to visualize temperature changes in the patient, as shown in FIG. 2A. For example, zone 200A is patterned with angled lines 210, while zone 200B is patterned straight lines 215. However, it should be appreciated that the fabric material/garment 10 may include any number of zones or regions 200A-X, which may include any desired pattern design therein. For example, as shown in FIG. 3, the sock 100 may be configured to include a plurality of adjacent regions or zones 200A-X, 210A-X, 220A-X, 230A-X, 240A-X, 250A-X, 260A-X, and 270A-X, which are defined by different shapes, and that include different patterns and which include different liquid crystal formulations. Additionally, in some cases, the regions 200A-X may be grouped within a plurality of larger primary groups 300A-X, such that each primary group 300A-X comprises a particular pattern or comprises a particular temperature range to which it is sensitive.

To evaluate the fabric 10 contemplated by the present invention, a commercially available fabric and cholesteric inks were used to demonstrate its operation. A sprayable and encapsulated liquid crystal material from HALCREST was used, such that this formulation transitions through its visible color range at temperatures between about 77° F. and 86° F. Specifically, the liquid crystal material was airbrushed on a black nylon fabric and allowed to dry. Draping of the fabric 10 on an individual's hand showed the color of the cholesteric coating 20 with the temperature profile shown as differences in color. The fabric was washed in water and reused with little or no degradation of the thermochromic response.

Therefore, one advantage of the present invention is that a thermochromic fabric may be treated with patterns of different cholesteric liquid crystal formulations, so that the fabric is able to detect temperature changes over a broad range with high sensitivity. Another advantage of the present invention is that a thermochromic fabric may include patterns of different cholesteric liquid crystal formulations, which can be used as a diagnostic tool that provides a visual temperature profile of all or a portion of a patient's body to identify various medical conditions.

Another advantage of the present invention is that a thermochromic fabric treated with cholesteric liquid crystal material may be configured to form a wearable garment, such as a form-fitting garment, such as a sock, shirt, pants, etc. to be worn by a patient.

Furthermore, while the discussion provided herein relates to the use of the thermochromic fabric/garment for diagnosing human patient, it is also contemplated that the present invention may be used for diagnosis of animals. It is also contemplated that the thermochromic fabric/garment may be used in any desired context where visual temperature monitoring is desired.

Thus, it can be seen that the objects of the present invention have been satisfied by the structure and its method for use presented above. While in accordance with the Patent Statutes, only the best mode and preferred embodiments have been presented and described in detail, with it being understood that the present invention is not limited thereto or thereby. Accordingly, for an appreciation of the true scope and breadth of the invention, reference should be made to the following claims.

What is claimed is:

1. A thermochromic garment comprising:
   a garment formed of a layer of fabric material;
   a first liquid crystal formulation provided by a first portion of said fabric; and
   a second liquid crystal formulation provided by a second portion of said fabric that is different from said first portion of said fabric, said second liquid crystal formulation positioned laterally adjacent to said first liquid crystal formulation, wherein said first and second formulations change color over different temperature ranges, and
   wherein said first liquid crystal formulation of said first portion is arranged in a first pattern, and said second liquid crystal formulation of said second portion is arranged in a second pattern different from said first pattern.

2. The thermochromic fabric of claim 1, wherein said layer of fabric material is black in color.

3. The thermochromic fabric of claim 2, wherein said layer of fabric material comprises nylon or a nylon/cotton blend.

4. The thermochromic fabric of claim 1, wherein said temperature ranges are adjacent to each other.

5. The thermochromic fabric of claim 1, wherein said liquid crystal formulations are spaced from the skin by said layer of fabric material.

6. The thermochromic fabric of claim 1, wherein said liquid crystal formulations each has a different liquid crystal concentration.

7. The thermochromic fabric of claim 1, wherein said liquid crystal formulations each has a different type of liquid crystal material.

8. The thermochromic fabric of claim 1, wherein said liquid crystal formulations each includes cholesteric liquid crystal material.

9. The thermochromic fabric of claim 1, wherein at least one of said liquid crystal formulations includes cholesterol esters.

10. The thermochromic fabric of claim 1, wherein said liquid crystal formulations coat threads of said layer of fabric material.

11. The thermochromic fabric of claim 1, wherein said liquid crystal formulations are positioned adjacent to said layer of fabric.

12. The thermochromic fabric of claim 1, wherein at least one of said liquid crystal formulations includes microcapsules of liquid crystal material.

13. The thermochromic fabric of claim 1, wherein said first portion has a shape that is different from a shape of said second portion.

14. The thermochromic fabric of claim 1, wherein said first portion and said second portion have a shape defined by said layer of fabric.

15. The thermochromic fabric of claim 1, wherein said first portion and said second portion cover an entire area of said garment.

16. The thermochromic fabric of claim 1, wherein said first and second liquid crystal formulations are carried upon a first surface of said layer of fabric, and wherein a second surface of said fabric layer, which is spaced apart from said first surface, is configured to be placed in direct contact with the skin.

17. The thermochromic fabric of claim 1, wherein said garment comprises a sock.

18. The thermochromic fabric of claim 1, wherein said fabric layer includes a plurality of threads, such that said first and second liquid crystal formulations are imbibed in said threads.

19. The thermochromic fabric of claim 1, wherein one or more of said first and second patterns include a plurality of geometric shapes.

20. The thermochromic fabric of claim 1, wherein said first and second patterns each include a plurality of zones, such that each said zone is sensitive to a different temperature range.

21. The thermochromic fabric of claim 20, wherein each said zone includes a different pattern.

* * * * *